US00PP17331P2

(12) United States Plant Patent
Harris

(10) Patent No.: US PP17,331 P2
(45) Date of Patent: Jan. 2, 2007

(54) ***AZALEA* PLANT NAMED 'MNIJ92'**

(50) Latin Name: ***Rhododendron* sp.**
Varietal Denomination: MNIJ92

(76) Inventor: James O. Harris, 538 Swanson Dr., Lawrenceville, GA (US) 30043

( * ) Notice: Subject to any disclaimer, the term of this patent is extended or adjusted under 35 U.S.C. 154(b) by 87 days.

(21) Appl. No.: 11/180,478

(22) Filed: Jul. 13, 2005

(51) Int. Cl.
*A01H 5/00* (2006.01)

(52) U.S. Cl. ..... Plt./240

(58) Field of Classification Search ..... Plt./240
See application file for complete search history.

*Primary Examiner*—Kent Bell
(74) *Attorney, Agent, or Firm*—Jondle & Associates P.C.

(57) ABSTRACT

A new variety of *Azalea* plant found as a seedling in a planned cross between the female hybrid *Azalea* 'EMBERS' and the male hybrid *Azalea* 'September Morn' is disclosed. The new variety possesses a unique blooming time and is very cold hardy. It is small, compact, dense and low-growing *Azalea* with attractive, single red flowers.

3 Drawing Sheets

Genus/species: *Rhododendron* sp.
Botanical designation: 'MNIJ92'.

BACKGROUND OF THE INVENTION

The present invention is a new and distinct variety of evergreen *Azalea* of the genus *Rhododendron*. This new *Azalea*, hereinafter referred to as 'MNIJ92', was discovered in March, 1999 in Lawrenceville, Ga. 'MNIJ92' originated from a planned hybridization between *Azalea* 'EMBERS' (U.S. Plant Pat. No. 10,581) and 'September Morn' (unpatented) in Lawrenceville, Ga. The value of this new cultivar lies in its unique blooming period, growth habit, and cold hardiness.

Asexual propagation of the new plant by cuttings was performed in Dearing, Ga. The new plant retains its distinctive characteristics and reproduces true to type in successive generations by vegetative propagation.

SUMMARY OF THE INVENTION

The following are the most outstanding and distinguishing characteristics of this new cultivar when grown under normal horticultural practices in Dearing, Ga.

1. Unique spring, summer and fall blooming;
2. Extremely long and floriferous bloom period (5–6 months with blooms);
3. Easily propagated by semi-hardwood cuttings in late spring through summer;
4. Slow growth rate under normal fertilization and moisture conditions;
5. Compact, dense, and low-growing nature;
6. Grows well in containers;
7. Thrives in shade or sun; and
8. Hardy in USDA Zone 7a.

DESCRIPTION OF THE PHOTOGRAPHS

This new *Azalea* hybrid variety is illustrated by the accompanying photographs which show blooms and foliage of the plant in full bloom. The colors shown are as true as can be reasonably obtained by conventional photographic means.

Figure 1:
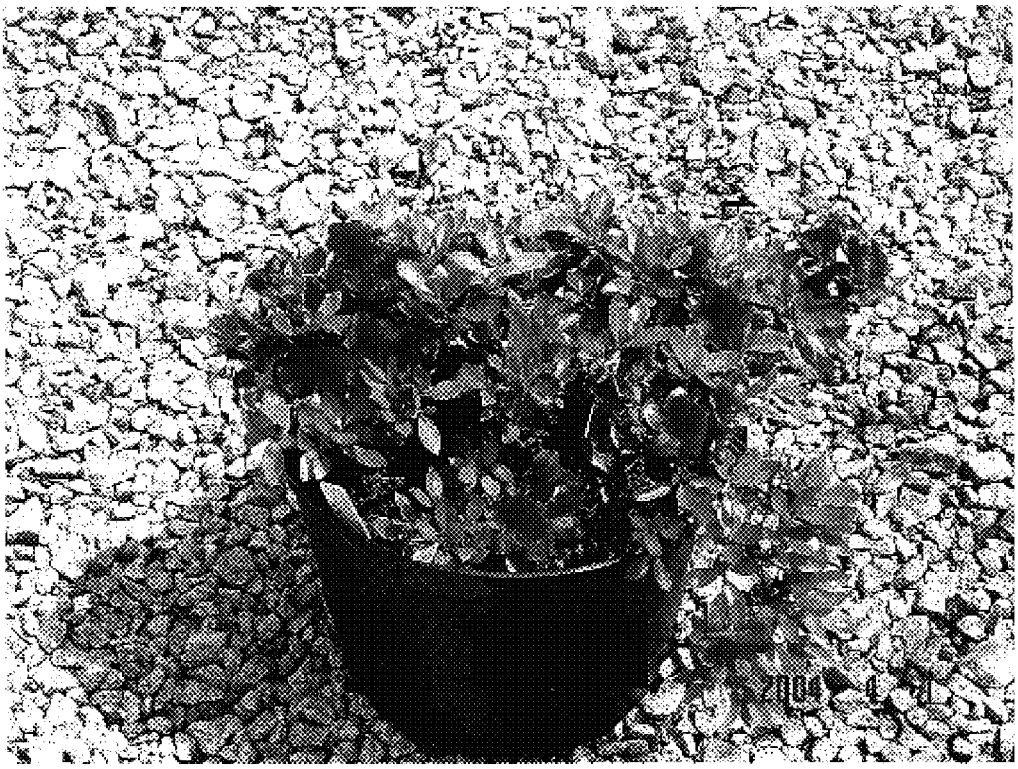

FIG. 1. shows growth habit and flowers of mature plant.

Figure 2:
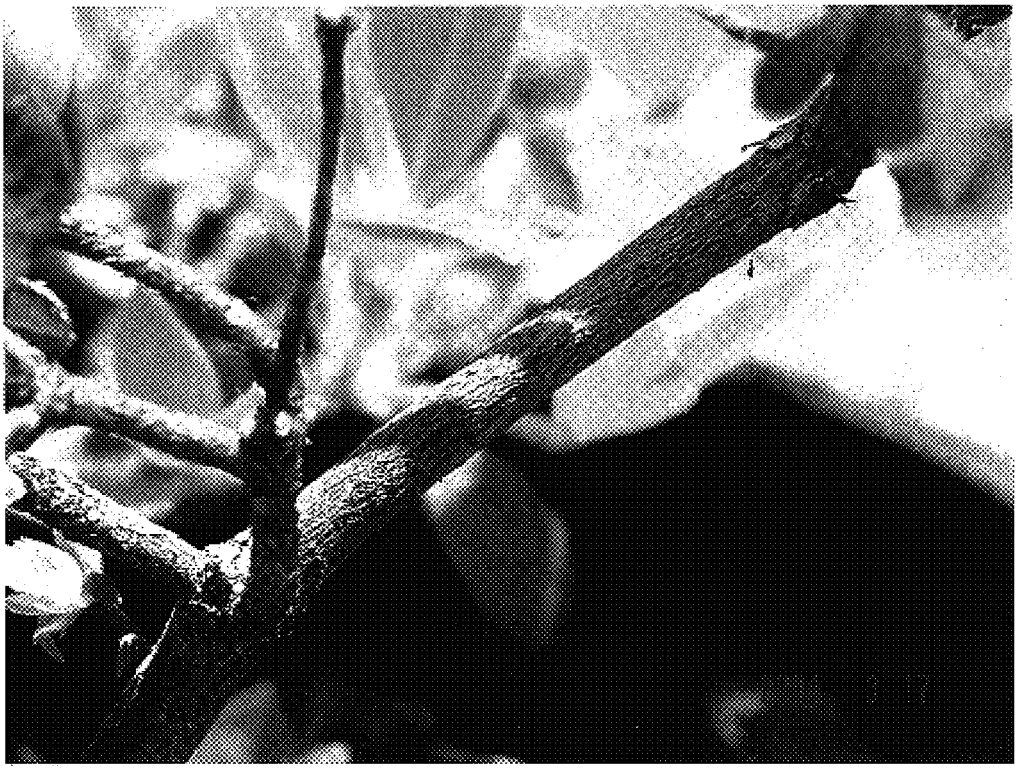

FIG. 2. shows a close-up view of stems.

Figure 3:
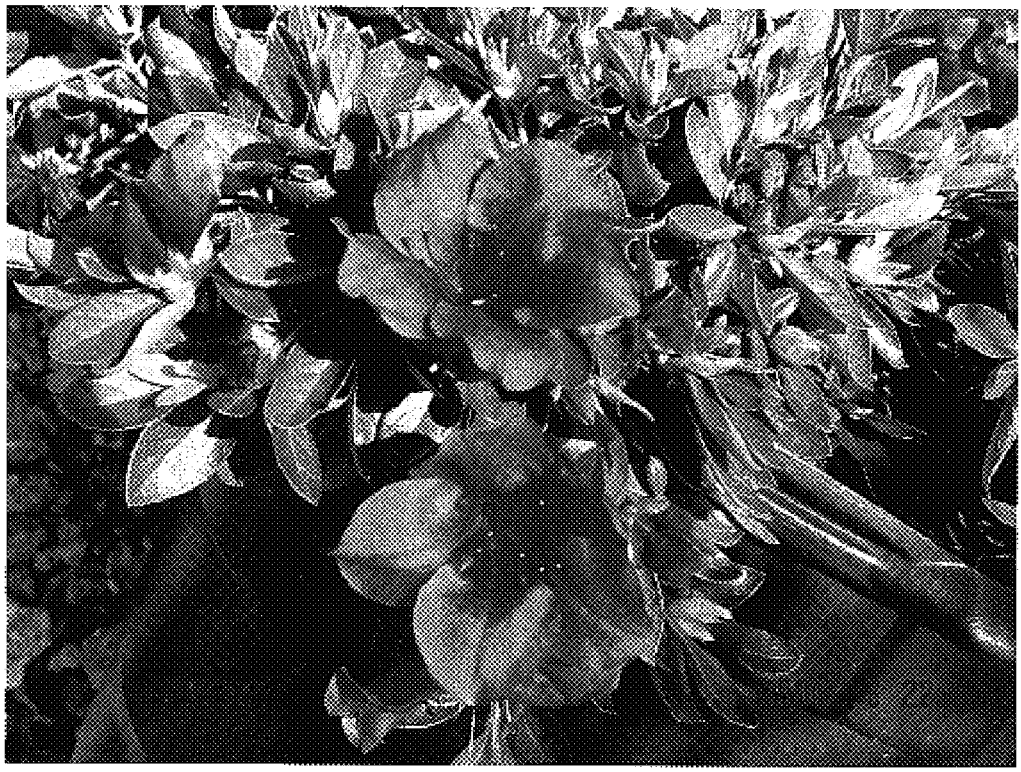

FIG. 3. shows a close-up view of mature foliage, flower buds and flowers.

Figure 4:
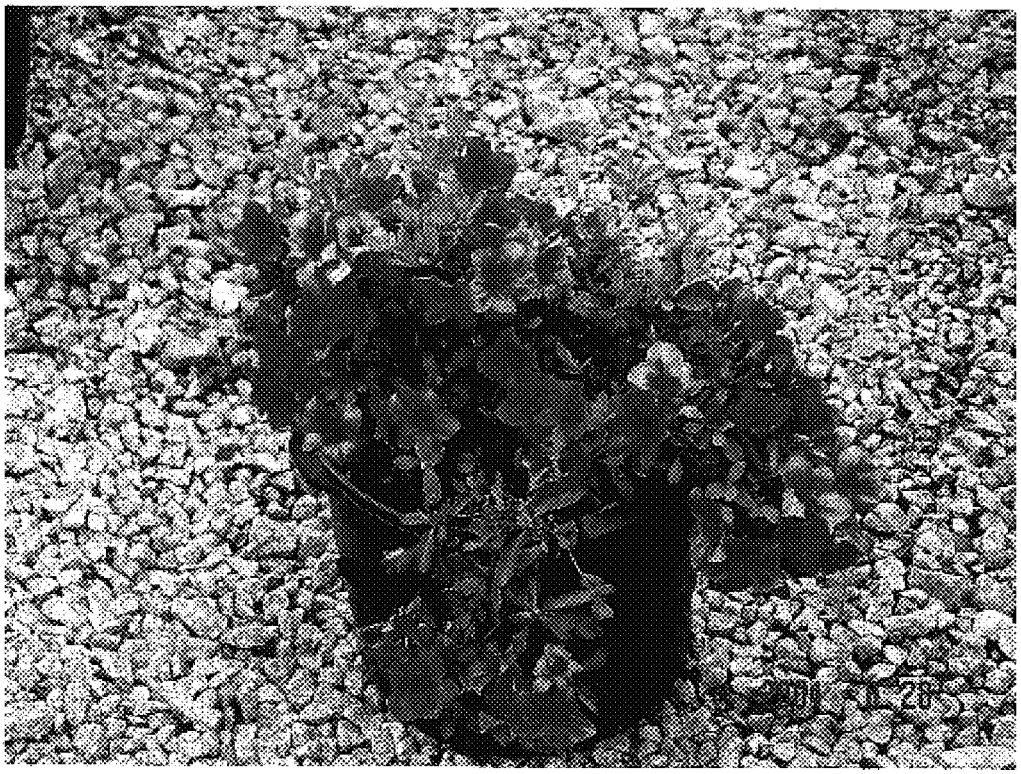

FIG. 4. shows the plant in full bloom.

Figure 5:
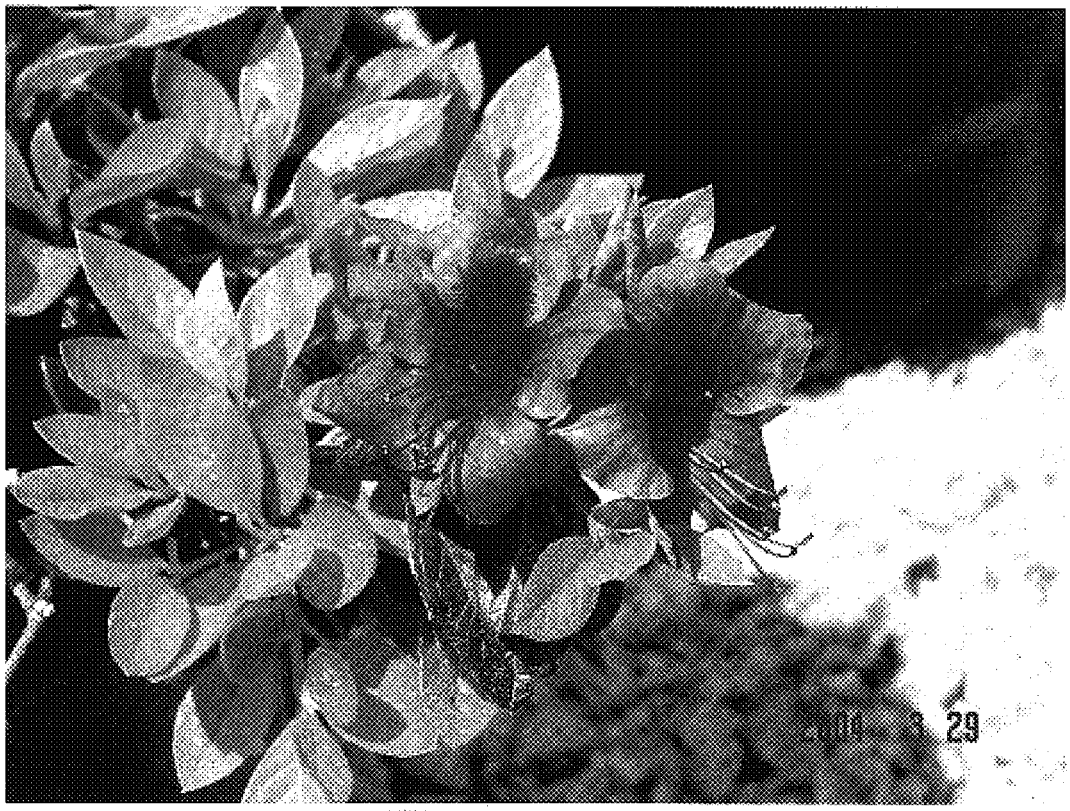

FIG. 5. shows a close-up view of several mature inflorescences.

DETAILED DESCRIPTION OF THE NEW PLANT

The following is a detailed description of the new variety of *Azalea* based on observations made of a 3-year-old plant grown in a seven-gallon container according to wholesale commercial production conditions in Dearing, Ga. The colors of the various plant parts are detailed with reference to The Royal Horticultural Society Colour Chart.

Classification:
- *Family.*—Ericaceae.
- *Species.*—*Rhododendron* sp.
- *Common name.*—*Azalea*.
- *Commercial name.*—'MNIJ92'.

Parentage:
- *Female parent.*—*Azalea* hybrid 'EMBERS' (U.S. Plant Pat. No. 10,581).
- *Male parent.*—Harris hybrid *Azalea* 'September Morn' (unpatented).

Growth:
- *Form.*—Small, compact, dense and low growing.
- *Height.*—6–9 inches.
- *Width.*—24 inches.
- *Growth habit.*—Compact, dense and low growing.
- *Growth rate.*—Slow growth rate under normal fertilization and moisture conditions. In a period of six years from a rooted cutting, the plant reaches a height of 12–18 inches and a spread of 24 inches. The growth rate is normally about 2 to 3 inches per year; the plant reaches a height of 24–36 inches at maturity while maintaining a dense habit due to the abundant branch development.

*Spring growth.*—In 2004, the date of initial spring growth was March 9, in Dearing, Ga. After the initial spring flush, there was continuous growth through the fall. The average length of terminal growth of the initial spring flush is about 1½ inches for a plant in full sun and about 1⅝ inches when grown in shade. This growth, if not pruned, will begin to produce flowers starting in mid to late March. As the plant continues to grow through summer and fall, more flower buds are produced which mature and bloom from mid June until frost. 'MNIJ92' bloomed until frost in December of 2003 in Dearing, Ga. The remaining growth produces about 1 to 2 inches of height.

*Life cycle.*—Perennial, evergreen.

Leaves:

*Leaves are evergreen.*—Leaf arrangement: Alternate, simple.

*Leaf shape.*—Broadly elliptic to obovate.

*Leaf length.*—1⅛ inches.

*Leaf width.*—9/16 inches.

*Leaf margin.*—Entire.

*Leaf base.*—Acuminate.

*Leaf apex.*—Mucronate.

*Petiole length.*—5/16 inch.

*Petiole color.*—RHS 146D (yellow-green).

*Mature leaf.*—Upper leaf surface: Surface texture: Semi-glossy. Surface color: RHS 147A (yellow-green). Surface pubescence: Slight. Surface pubescence color: RHS 155C (white). Midveins and laterals: Impressed on surface. Lower leaf surface: Surface texture: Matte. Surface color: RHS 146B (yellow-green). Surface pubescence: Moderate. Surface pubescence color: RHS 155C (white). Midveins and laterals: Prominent on surface.

*Immature leaf.*—Upper leaf surface: Surface texture: Matte. Surface color: RHS 144A (yellow-green). Surface pubescence: Strigose. Surface pubescence color: RHS 155C (white). Lower leaf surface: Surface texture: Matte. Surface color: RHS 146B (yellow-green). Surface pubescence: Strigose. Surface pubescence color: RHS 155C (white). Immature petioles and midveins: Petiole color: RHS 144A (yellow-green). Midvein color: RHS 144A (yellow-green). Petiole pubescence: Strigose. Petiole pubescence color: RHS 155C (white). New growth pubescence: Strigose. Length of pubescence: 1/32 to 1/16 inch; numerous on mid-vein and petiole, more so as the leaf matures.

Stems:

*Densely branched.*—Young stems: Stem color: RHS 144B (yellow-green). Stem pubescence: Strigose. Stem pubescence color: At point of attachment hairs emerge RHS 155C (white) and mature to RHS 165B (greyed-orange); hairs distal from stem are RHS 166D (greyed-orange). Bark color of mature first-year stem: RHS N199C (greyed-brown). Stem length: 1½ to 3 inches. Stem diameter: 3/32 to ⅛ inch.

*Second-year stems.*—Bark color: RHS 200A (brown). Stem pubescence: Glabrous and rugose. Stem length: 1½ to 2½ inches. Stem diameter: ⅛ inch.

*Pith.*—Solid and uniform.

*Internode length.*—Grown in full sun: 1/16 inch to ¾ inch. Grown in light shade: 1/16 inch to ⅝ inch.

Flower buds:

*Buds.*—Tight; borne in groups of two or three; sheathed by a pair of modified leaf bracts.

*Bud shape.*—Ovate and acuminate.

*Bud size.*—½×¼ inch.

*Bud scales.*—Distal portion is pubescent, individual hairs emerge RHS 155C (white) and mature to RHS 167C (greyed-orange).

*Bud color.*—RHS 144B and RHS 145D (yellow-green).

*Bud sheath.*—Bud sheath length: 7/16 to 17/32 inch long. Immature sheath color: RHS 144A (yellow-green) and RHS 145D (yellow-green). Mature sheath color: As the buds swell, the bud sheath matures from RHS 144A and RHS 145D (yellow-green) to RHS 180B (greyed-red), falls off, and reveals the flower color of RHS 53C (red).

*Bud pedicel.*—Pedicel length: 3/16 inch long. Pedicel color: RHS 144A (yellow-green). Pedicel pubescence: Strigose. Pedicel pubescence color: RHS N155D (white).

*Calyx.*—Calyx shape: Cup-shaped, persistent. Size: ¼ to 7/16 inch long. Color: RHS 144A (yellow-green). Pubescence: Strigose. Calyx pubescence color: RHS N155D (white).

Flowers:

*Flower type.*—Single, perfect.

*Flowering habit.*—Borne on the current season's growth.

*Lastingness of flowers on the plant.*—6–8 days in the garden.

*Length of flowering period.*—3 to 4 weeks in March and April; flowering resumes in June and continues until frost, which can be as late as November or December in Dearing, Ga.

*Peduncle length.*—⅛ to ½ inch.

*Shape.*—Open funnel-shaped.

*Flower diameter.*—2 to 2½ inches.

*Flower depth.*—1½ inches.

*Petal number.*—5, fused at the base and remain fused up to 1 inch from the base.

*Petal pubescence.*—Glabrous.

*Petal shape.*—Elliptic to obovate with rounded apices and entire margins.

*Petal size.*—1½ inches long×1 inch wide.

*Petal color.*—Upper and lower surfaces: RHS 53C (red). Spots on 3 of the five petals: RHS 53A (red).

*Sepals.*—Ovate and joined at the base to form a cup.

*Sepal number.*—5.

*Sepal color.*—RHS 144A (yellow-green).

*Sepal size.*—¼ inch long×⅛ inch wide.

Reproductive organs:

*Ovary.*—Extremely tomentose.

*Placenta arrangement.*—5 locules.

*Pistil.*—Single, non-petaloid.

*Pistil length.*—1¼ to 1½ inches long.

*Stigma color.*—RHS 58A (red-purple).

*Style color.*—RHS 58B (red-purple).

*Stamen number.*—5, non-petaloid.

*Stamen length.*—1 5/16 to 1 9/16 inches.

*Stamen color.*—Filaments: RHS 57A (red-purple). Anthers: RHS 176A (greyed-orange).

*Pollen color.*—RHS 155B (white).

*Fragrance.*—None.

CULTURE

'MNIJ92' grows well in a wide range of conditions and tolerates sun to shade. It prefers moist, well-drained soil that is rich in organic matter and responds well to mulching and medium applications of fertilizer. It does best in soil with a pH of 5.0 to 5.5. 'MNIJ92' is adaptable to container and above ground planters; it also makes a good foundation plant and requires very little pruning. It is propagated with semi-hardwood cuttings in late spring through summer.

DISEASES/INSECTS

Lace bugs and spider mites can be a problem.

COMPARISON WITH PARENTAL CULTIVARS

The female, or seed parent, of 'MNIJ92' is the hybrid *Azalea* 'EMBERS' (U.S. Plant Pat. No. 10,581) which has strong red, single/semi-double flowers, blooms both early and late seasons, and is a globose-shaped plant. 'EMBERS' is the result of a cross between the moderately pink Robin Hill hybrid *Azalea* 'Watchet' (unpatented) and the orange-red *Rhododendron oldhamii* 'Fourth of July' (unpatented).

The male, or pollen, parent is Harris hybrid 'September Morn' (unpatented) which is a dense and upright growing, early and late blooming *azalea* with single, red blooms. 'September Morn' is the result of a cross between the red blooming Gartrell hybrid 'Cherie' (unpatented) and the yellowish pink blooming Gable hybrid 'Indian Summer' (unpatented).

In Table 1 below, the instant plant is shown in comparison with the parental cultivars.

TABLE 1

| Characteristic | 'MNIJ92' | 'EMBERS' | 'September Morn' |
|---|---|---|---|
| Height (Mature) | 24–36 in. | 4–5 ft. | 2½ ft. |
| Width (Mature) | 24 in. | 5–6 ft. | 3 ft. |
| Flower Diameter | 2–2½ in. | 2½–2¾ in. | 2–2½ in. |
| Flower Form | Single | Single/semi-double | Single |
| Flower Color | RHS 53C (red) | RHS 44A (red) | RHS 48A (red) |
| Flowers per Terminal | 2 or 3 | 2–3 | 2 |
| Bloom Period | Mid to late March to early April; Mid-June to frost | April; Late July to frost | Early April; September to frost |
| Petal Number | 5 | 5–14 | 5 |
| Hardy Zone | 7a | 7 | 5 |
| Stamen Number | 5 | 0–9 | 5 |
| Stamen Type | Non-petaloid | Some petaloid | Non-petaloid |

What is claimed is:

1. A new variety of *Azalea* plant named 'MNIJ92' as herein shown and described.

* * * * *